(12) United States Patent  
Kim et al.

(10) Patent No.: US 7,859,670 B2  
(45) Date of Patent: Dec. 28, 2010

(54) SYSTEM AND METHOD FOR DETECTING FLUORESCENCE IN MICROFLUIDIC CHIP

(75) Inventors: Suhyeon Kim, Seoul (KR); Jintae Kim, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 462 days.

(21) Appl. No.: 11/872,384

(22) Filed: Oct. 15, 2007

(65) Prior Publication Data

US 2008/0192254 A1 Aug. 14, 2008

(30) Foreign Application Priority Data

Feb. 8, 2007 (KR) .................. 10-2007-0012996

(51) Int. Cl.
*G01N 21/25* (2006.01)

(52) U.S. Cl. ...................................... 356/417
(58) Field of Classification Search ................ 356/417, 356/436; 250/458.1–461.2
See application file for complete search history.

(56) References Cited

U.S. PATENT DOCUMENTS

| | | | |
|---|---|---|---|
| 5,928,907 A | 7/1999 | Woudenberg et al. | |
| 6,369,893 B1 | 4/2002 | Christel et al. | |
| 6,399,952 B1 | 6/2002 | Maher et al. | |
| 7,081,226 B1 | 7/2006 | Wittwer et al. | |
| 2003/0222222 A1 | 12/2003 | Dong et al. | |
| 2004/0224317 A1 | 6/2004 | Korodunsky et al. | |
| 2006/0006067 A1* | 1/2006 | Unger .................. | 204/452 |

FOREIGN PATENT DOCUMENTS

| | | |
|---|---|---|
| JP | 2003004636 | 1/2003 |
| JP | 2003028798 | 1/2003 |
| JP | 2005030784 | 2/2005 |
| KR | 1020010013682 | 2/2001 |
| KR | 1020030037314 | 5/2003 |

* cited by examiner

*Primary Examiner*—Tarifur Chowdhury  
*Assistant Examiner*—Abdullahi Nur  
(74) *Attorney, Agent, or Firm*—Cantor Colburn LLP (57) ABSTRACT

A system and a method for detecting fluorescence in a microfluidic chip having a microchamber and measuring the amount of the fluorescence are disclosed. In the system and method, an optical device detects fluorescence generated by a fluorescent material. The position of the outer circumference of a microfluidic chip is identified based on the change of the amount of the detected fluorescence. Then, the position of a microchannel is calculated based on the position of the outer circumference of the microfluidic chip and the distance between the outer circumference and the microchamber. Hence, the amount of the fluorescence only generated from the microchamber of the microfluidic chip is automatically calculated. Further, a plurality of samples can be analyzed at the same time, thereby reducing analysis time and cost.

17 Claims, 5 Drawing Sheets

SYSTEM AND METHOD FOR DETECTING FLUORESCENCE IN MICROFLUIDIC CHIP

CROSS-REFERENCES TO RELATED APPLICATIONS

The present invention claims priority of Korean patent application number 10-2007-0012996, filed on Feb. 8, 2007, which is incorporated by reference in its entirety.

BACKGROUND OF THE INVENTION

1. Field of the Invention

The present invention relates to a fluorescence detection system, which detects fluorescence in a microfluidic chip having a microchamber and measures the amount of the fluorescence. In addition, the present invention relates to a method for detecting fluorescence in microfluidic chip having a microchamber and measuring the amount of the fluorescence.

In the fluorescence detection system of the present invention, an optical device detects fluorescence generated by a fluorescent material. The position of the outer circumference of a microfluidic chip is identified based on the amount of the detected fluorescence. Then, the position of a microchannel is calculated based on the position of the outer circumference of the microfluidic chip and the distance between the outer circumference and the microchamber. Hence, the amount of the fluorescence only generated from the microchamber of the microfluidic chip is automatically calculated. Further, a plurality of samples can be analyzed at the same time, thereby reducing analysis time and cost.

2. Description of the Related Art

A microfluidic chip is fabricated by forming microchannels on a first substrate by micromachining such as photolithography, hot embossing and molding, and bonding a second substrate on the first substrate. Therefore, so that a very small amount of fluid can be contained and controlled in the chip. The advantage of this microfluidic chip is that the amount of reagent to be spent and analysis time can be reduced.

A microchamber in the microfluidic chip is a space that stores a material to be detected, which is introduced through an inlet and a microchannel. The width of the microchamber is larger than or equal to that of the microchannel. The width of the microchannel is usually several tens or hundreds of micrometers.

Fluorescence detection in the microchamber can be adopted in monitoring biochemical reactions such as Polymerase Chain Reaction (PCR), enzyme reaction or immunity analysis, in which the amount of fluorescence changes.

In PCR, denaturation, annealing and extension are performed at different temperatures, and such a temperature cycle can be iteratively conducted to amplify DNA.

There are several methods for monitoring the PCR process in real-time, most of which adopt the fluorescence detection at present.

Various methods have been introduced for the fluorescence detection. In one example, a dye such as SYBR Green I is bonded to double helix DNA, created by PCR, in order to enhance fluorescence. Another example is TaqMan® method. In this method, a DNA sequence capable of being bound between two primers is used as a probe except for primers which are used in PCR, and a fluorophore and a quencher are bound to both ends of the probe.

When cutting the probe using exonuclease activity of Taq polymerase used in DNA synthesis, the DNA bound between the fluorophore and the quencher is cut, and thus, the bond between the fluorophore and the quencher is broken. At this time, the emitted fluorescence is analyzed.

However, there are problems in that apparatuses used in the fluorescence detection should be precisely operated to obtain correct results.

SUMMARY OF THE INVENTION

The present invention relates to a system and a method for detecting fluorescence in a microfluidic chip.

According to an aspect of the present invention, there is provided a fluorescence detection system for detecting fluorescence in the microfluidic chip having a microchamber.

More particularly, the fluorescence detection system of the present invention comprises a chip mount for placing the microfluidic chip thereon; an optical device for emitting light on the microfluidic chip and detecting fluorescence which is generated from a fluorescent material existing in the microfluidic chip; a carriage for transporting the chip mount or the optical device at a predetermined speed, so that the optical device emits the light on the microfluidic chip while scanning the microfluidic chip; a measuring unit for measuring an optical signal detected by the optical device and converting the optical signal into a digital signal; and a calculator for calculating the amount of the fluorescent material in the microfluidic chip based on a measured value.

In the fluorescence detection system, the calculator identifies the position of the outer circumference of the microfluidic chip from the optical signal, detected by the optical device and the measuring unit, and calculates each position of the microchambers based on the position of the outer circumference, distance between the outer circumference and the microchamber, and distance between the microchambers. The measuring unit calculates a portion of the optical signal, which is generated from the microchambers of the microfluidic chip, based on the calculated position of the microchambers, and sends a calculated value of the optical signal to the calculator.

Here, the calculator is generally a personal computer, and the measuring unit is an electronic circuit that is internally mounted in the fluorescence detection system. A measurement value, which is converted into digital data, is transmitted through the communication between the calculator and the measuring unit.

Since the measurement value obtained by scanning the microfluidic chip is massive. Therefore, the measurement value data, if directly transmitted to the calculator, can cause a problem in communication speed in some cases such as PCR real-time fluorescence detection, in which measurement should be carried out plural times according to cycles. For example, in the case where 5,000 data are obtained by one scan per second, 15 Kbytes are necessary for one scan per second if the digital value of one data is of 24 bits. If this value is applied to six (6) channels, the measuring unit should send signals of 90 Kbytes per second to the calculator. This decelerates communication speed, and the calculator spends mole time to process the signals.

However, the present invention overcomes this problem by transmitting the detection signal of each microchamber as one data value. Then, even if the data value is 32 bit, data transmission for the eight microchambers and the six channels can be enabled by 192 bytes. Accordingly, the present invention can reduce the amount of data to be transmitted as well as is advantageous in terms of communication and calculation.

According to another aspect of the present invention, there is provided a method for detecting fluorescence in a microfluidic chip having at least one microchamber. The fluorescence detection method of the present invention includes steps of: injecting a sample and a fluorescent dye into the microchamber; emitting light from an optical device capable of detecting fluorescence, while transporting the microfluidic chip or the optical device, and detecting fluorescence generated by a fluorescent material existing in the microfluidic chip; and calculating the amount of the fluorescent material in the microfluidic chip based on the amount of the fluorescence detected by the optical device.

Here, the step calculating the amount of the fluorescent material includes: identifying a position of an outer circumference of the microfluidic chip based on an optical signal detected by the optical device; calculating a position of the microchamber based on the position of the outer circumference and a distance between the outer circumference and the microfluidic chamber; and extracting and summing portions of the optical signal generated by the microchamber of the microfluidic chip.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THEE PREFERRED EMBODIMENT

The present invention will now be described more fully with reference to the accompanying drawings, in which preferred embodiments thereof are shown. However, it should be understood that the present invention is not limited by the embodiments.

Figure 1A:
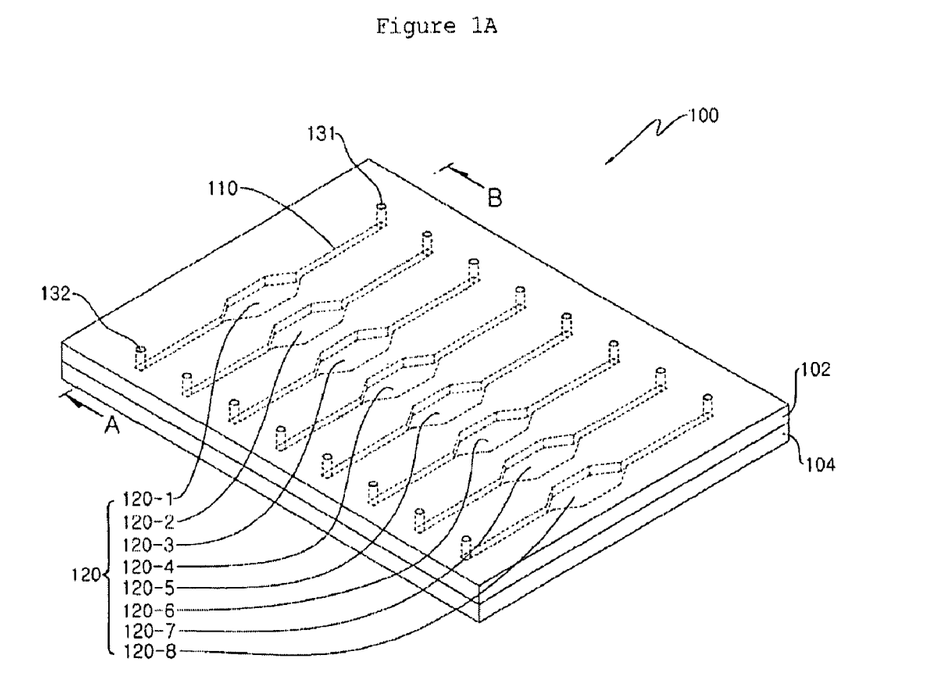
FIGS. 1A and 1B are perspective and cross-sectional views illustrating a microfluidic chip used in a fluorescence detection system according to the present invention, respectively.
Figure 1B:
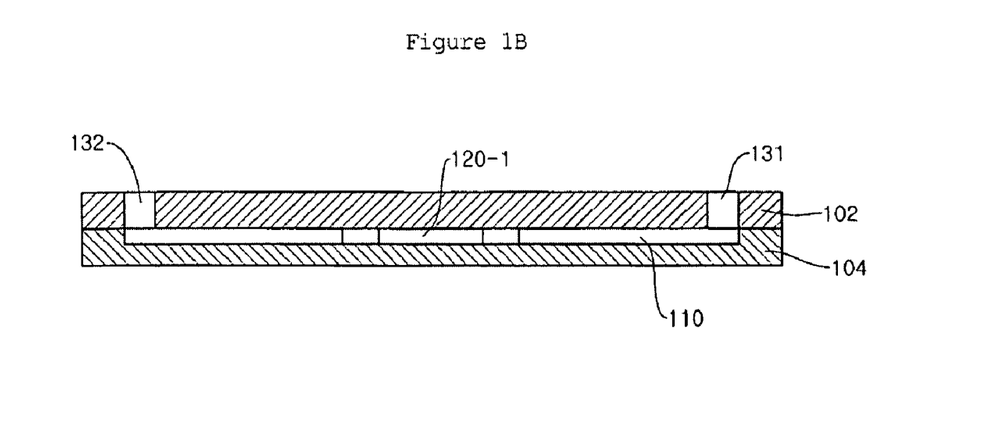

FIG. 1A is a perspective view illustrating a microfluidic chip 100 used in a fluorescence detection system according to an embodiment of the present invention, and FIG. 1B is a cross-sectional view taken along the line A-B in FIG. 1A.

The microfluidic chip 100 includes a plurality of microchambers 120, microchannels 110, inlets 131 and outlets 132. When a sample is injected into the chip 100 through the inlets 131, it enters the microchamber 120 through the microchannels 110 and remains in the microchamber 120.

The microchip 100 can be fabricated by bonding an upper substrate 102, in which the inlets 131 and the outlets 132 are engraved, to a lower substrate 104, in which the microchannels 110 and the microchambers 120 are engraved.

Figure 2:
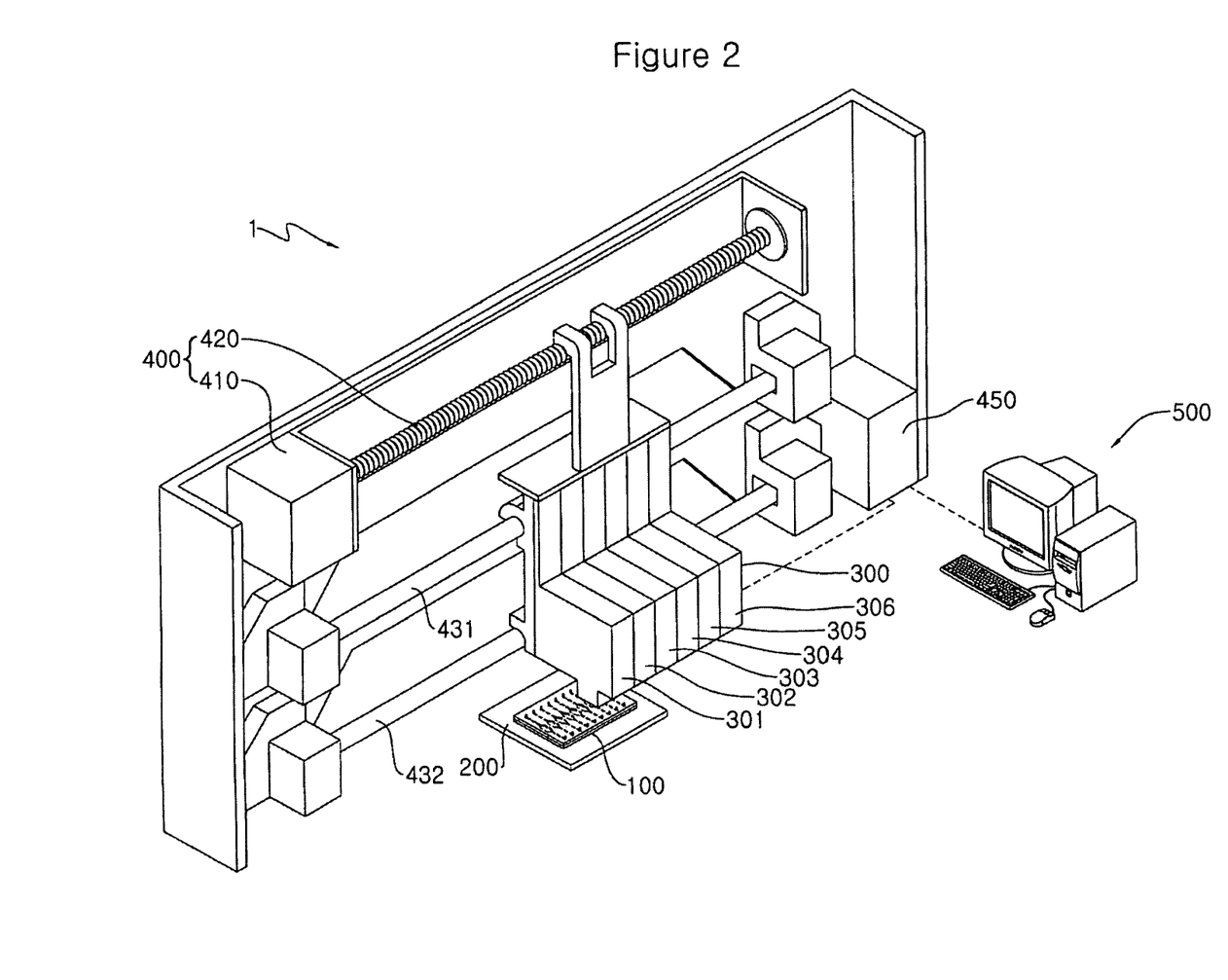
FIG. 2 is a perspective view schematically illustrating the fluorescence detection system according to the present invention.

FIG. 2 is a perspective view schematically illustrating the fluorescence detection system 1 according to the embodiment of the present invention.

The fluorescence detection system 1 includes a chip mount 200, an optical device 300, a carriage 400, a measuring unit 450 and a calculator 500. The microfluidic chip 1100 is placed on the chip mount 200. The optical device 300 emits light on the microfluidic chip and detects fluorescence, which is generated from a fluorescent material existing in the microfluidic chip 100. The carriage 400 transports the optical device 300 at a predetermined speed so that the optical device 300 can emit light while scanning the microfluidic chip. The measuring unit 450 converts optical signals, received from the optical device 300, into digital signals. The calculator 500 calculates the amount of the fluorescent material in the microfluidic chip 100 based on) the optical signals.

This embodiment has been described with respect to the case in which the carriage 400 transports the optical device. Alternatively, the carriage 400 can be designed to transport the chip mount 200. In any cases, the optical device 300 can emit light while scanning the microfluidic chip 100 in order to detect fluorescence.

In this embodiment, the carriage 400 includes an auger 420 and a motor 410 for rotating the auger 420 to a predetermined angle. As the motor 410 rotates the auger 420 to the predetermined angle, the optical device 300 coupled with the auger 420 can linearly move along guides 431 and 432.

For example, in the case where the auger 420 has a pitch 3 mm and the motor 410 is a stepping motor having a rotation angle 18° per step, the motor is driven 20 steps and the auger 420 is rotated once (i.e., auger 420 rotates 360°), so that the optical device moves 3 mm. Therefore, when the motor is driven one step, the optical device moves 150 μm In the case where the motor is driven micro-steps, it is possible to control the optical device to move to a smaller distance.

As the optical device 300 can linearly move as above, it can detect fluorescence in the microchambers 120-1 to 120-8 of the microfluidic chip 100 while sequentially scanning the same. In particular, if the fluorescence is detected at every time where the motor is driven one step, the optical device can move to a predetermined distance at the every time of one step driving, and thus the fluorescence in the microfluidic chamber can be detected at every specific distance.

The optical device 300 includes a plurality of optical elements 301 to 306, each of which emits a unique wavelength of light.

Figure 3:
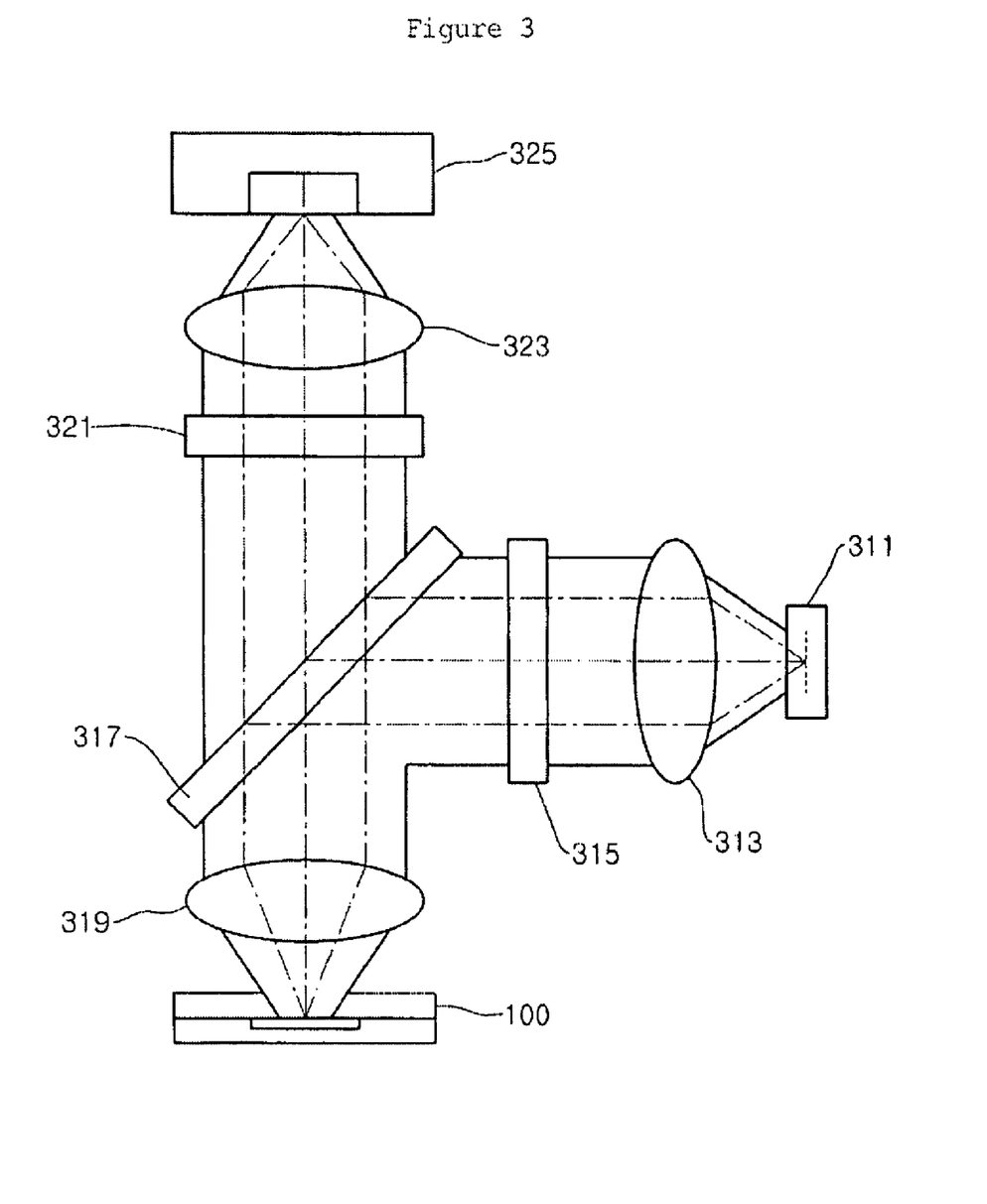
FIG. 3 is a conceptual view schematically illustrating the optical device for detecting fluorescence by emitting light onto a microfluidic chip in the fluorescence detection system according to the present invention.

FIG. 3 schematically illustrates the optical element 301 of the optical device 300 in the fluorescence detection system, which detects fluorescence by emitting light to the microfluidic chip.

A light source 311 (e.g., an LED light source) of the optical element 301 generates light, and an incident light adjustment lens 313 collimates the light to be similar to parallel light. Then, an incident light filter 315 selectively transmits a short wavelength component of the light while removing long wavelength components of the light that would otherwise be erroneously detected as a fluorescent wavelength. After the light has passed through the incident light filter 315, it is reflected by a spectrometer mirror 317 that reflects short wavelength light, and then is condensed by an object lens 319 to the microfluidic chip 100.

When fluorescence is generated from the fluorescent material existing in the microfluidic chip 100, it is adjusted by the object lens 319 to be similar to parallel light and passes through the spectroscope mirror 317 capable of transmitting long wavelength light. Next, the fluorescence passes through a fluorescence filter 321, which can selectively transmit long wavelength light, in order to minimize the amount of light that would act as noise. Then, the fluorescence is condensed by a fluorescence adjusting lens 323, and is detected by a fluorescence detector 325 such as a photodiode.

The optical elements 301 to 306 can emit different and unique wavelength lights to detect the fluorescence by suitably selecting the light sources used therein and the transmitting wavelength bands of the incident light filter and the fluorescence filter. In the case where a plurality of fluorescent dyes, each of which generates unique wavelength light, is added to one microfluidic chip 100, it is possible to simultaneously detect fluorescences in a plurality of wavelength bands using the optical device.

Figure 4:
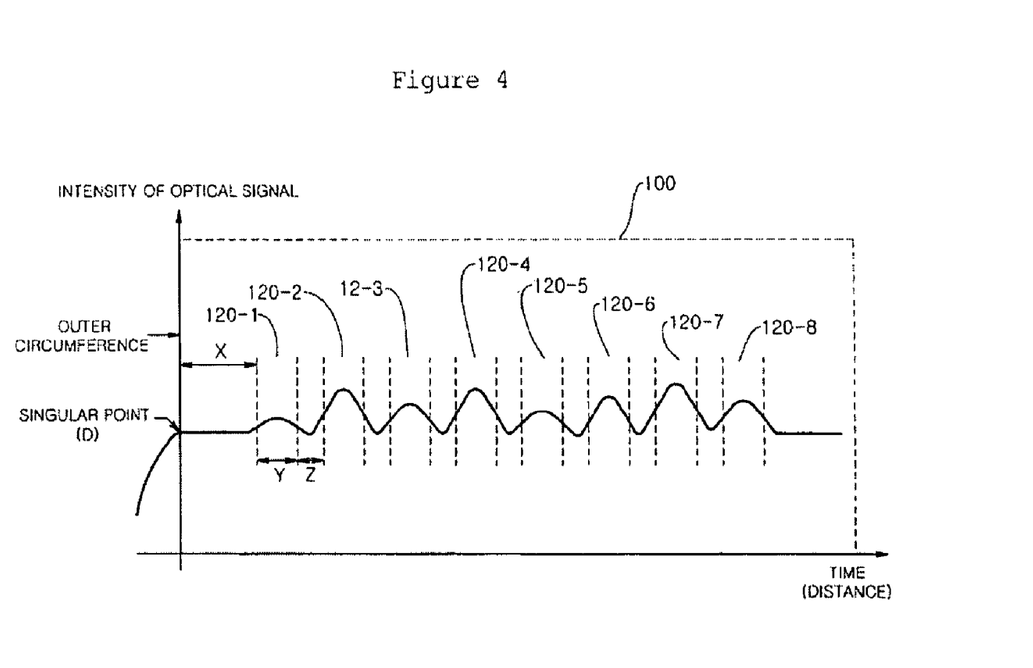
FIG. 4 is a graph illustrating the amount of fluorescence in the microfluidic chip, which is detected using fluorescence detection system according to the present invention.

FIG. 4 is a graph of optical signals from the microfluidic chip shown in FIG. 1, which are detected using the fluorescence detection system of the present invention.

The fluorescence detection system according to the present invention detects optical signals from the microfluidic chip while sequentially scanning the chip from outside to inside. Here, the intensity of the detected optical signals drastically changes on the outer circumference of the microfluidic chip 100. This is because the intensity of the optical signals detected from outer portions of the microfluidic chip 100 is different from that detected from inner portions of the microfluidic chip 100.

In the intensity distribution as shown in FIG. 4, the intensity of the optical signals drastically changes at a point 1) (hereinafter will be referred to as "singular point"). The point D is regarded as the position of the outer circumference of the microfluidic chip by the calculator 500.

In the case where the chip mount 200, on which the microfluidic chip 100 is placed, is made of a transparent material, or a mirror is attached to the surface of the chip mount 200, the intensity of the detected optical signals more drastically changes on the outer circumference of the microfluidic chip 100. This is because the intensity of the optical signals detected from the outer portions (i.e., a transparent portion or a mirror portion) of the microfluidic chip 100 shows a larger difference from that detected from the inner portions of the microfluidic chip 100. Therefore, the calculator 500 can more easily identify the singular point (i.e., the position of the outer circumference of the microfluidic chip) by analyzing the detected optical signals.

Using the position of the outer circumference located as above, the distances X between the outer circumference and the microchambers which is fixed according to the microfluidic chip structure, the widths Y of the microchambers, and the intervals Z between the microchambers, the positions of the microchambers 120-1 to 120-8 can be calculated.

Since the transport speed of the optical device 300 is constant, it is also possible to calculate transport time that is spent until the optical device 300 is transported to this position. Using the positions of the microchambers and/or the scanning time of the microchambers, which are calculated as above, it is possible to automatically calculate the amount of fluorescence, which is generated from only the microchambers 120-1 to 120-8 of the microfluidic chip 100.

Once the position of the outer circumference of the microfluidic chip is acquired by scanning, the optical device can utilize the already-acquired position information of the outer circumference of the microfluidic chip when scanning the microfluidic chip again in order to identify the reaction process after a predetermined time period. Therefore, the amount of fluorescence can be quickly calculated.

Hereinafter, the experiment of measuring the amount of fluorescence in a sample using the fluorescence detection system according to the embodiment of the present invention and its result will be described.

In the optical element 301 of the optical device 300 of the fluorescence detection system 1 used in the experiment, the light source 311 was a blue LED having a peak wavelength 470 nm, the incident light filter 313 was a short wavelength pass filter having a center wavelength 495 nm, the spectrometer mirror 317 had a center wavelength 505 nm, and the fluorescence filter 321 was a long wavelength pass filter having a center wavelength 510 nm. The object lens 319 was JDI580 available from Juraron, and the fluorescence detector 325 was S1227-33BR photodiode available from Hamamatsu.

In the optical device 301, the quantity of light passing through the object lens 319 was about 0.5 mW, a signal detected by the photodiode of the fluorescence detector 325 was converted from a current signal into a voltage signal through an amplification circuit having an output gain of $10^9$, which was then recorded by a digital oscilloscope (not shown).

The microfluidic chip 100 was fabricated so as to have eight (8) microchambers 320. The interval between the microchambers 320 was 1.5 mm, the width of the microchamber 320 was 1 mm, and the depth of the microchamber 320 was 200 μm.

Among the total eight microchambers, three (3) microchambers 320-2, 320-4 and 320-6 were filled with 100 mM sodium borate buffer solution (pH 9.5), and the remaining five (5) microchambers were filled with 50 uM fluorescein standard solution available from Invitrogen, which was diluted with 100 mM sodium borate buffer solution (pH 9.5).

Figure 5:
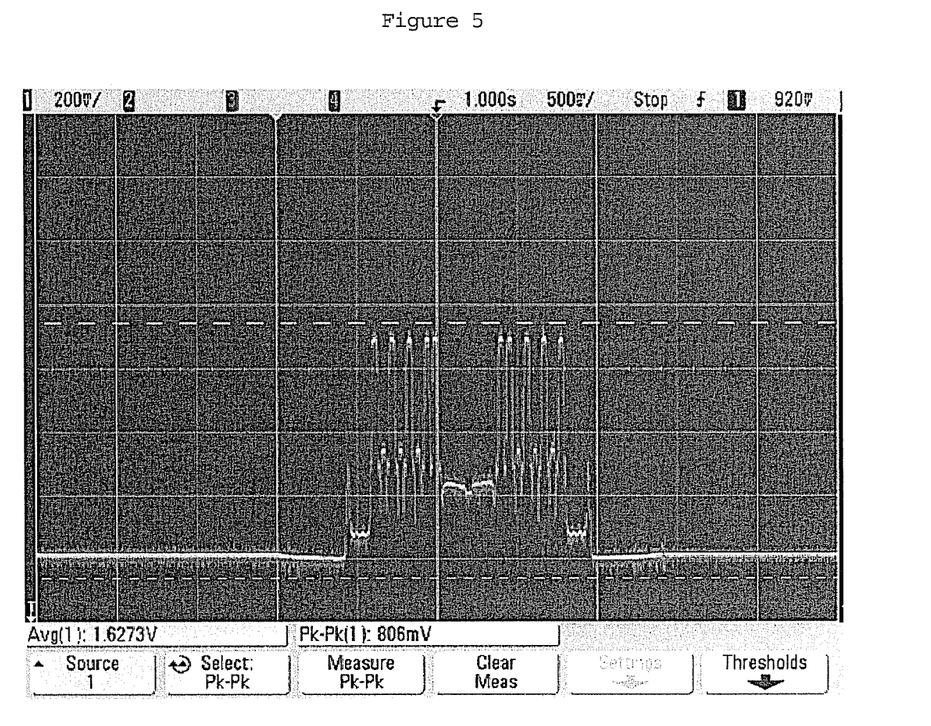
FIG. 5 is a graph illustrating a result of measuring the amount of fluorescence, which is obtained by the fluorescence detection system according to the present invention, using an oscilloscope.

The motor 410 was driven ¼ micro-step at 1000 Hz, thereby reciprocating the optical device 300. FIG. 5 is the result of the above experiment, obtained by measuring the amount of fluorescence using the oscilloscope. As shown in FIG. 5, sixteen (16) peaks were detected, which were laterally symmetrical to each other. She peaks are signals that the optical device 300 detected from fluorescent signals exiting the microchambers of the microfluidic chip when the optical device 300 was reciprocating on the microfluidic chip.

Figure 6:
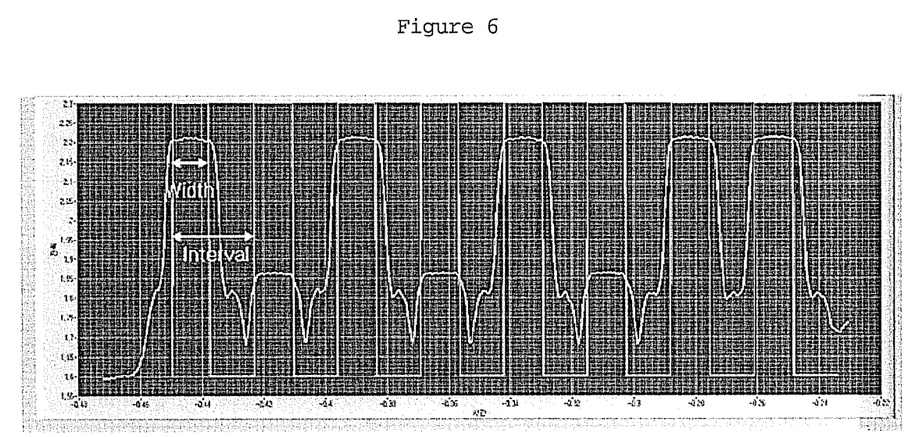
FIG. 6 is a graph illustrating the result of FIG. 5, averaged per millisecond.

FIG. 6 is a graph illustrating the result of FIG. 5, averaged per millisecond. Referring to FIG. 6, the uniform interval between the lines indicates a region where the fluorescence signals exiting the microchambers can be summed up (i.e., the width of the microchambers). The amount of fluorescence of a respective microchamber can be indicated with a single value by summing up the optical signals in this region.

While the present invention has been described with reference to the particular illustrative embodiments and the accompanying drawings, it is not to be limited thereto. It is to be appreciated that those skilled in the art can substitute, change or modify the embodiments in various forms without departing from the scope and spirit of the present invention.

What is claimed is:

1. A fluorescence detection system for detecting fluorescence in a microfluidic chip having at least a microchamber, comprising: a chip mount upon which the microfluidic chip is placed; an optical device which emits light on the microfluidic chip and detecting fluorescence which is generated from a fluorescent material existing in the microfluidic chip; a carriage which transports the chip mount or the optical device at a predetermined speed, so that the optical device emits the light on the microfluidic chip while scanning the microfluidic chip; a measuring unit which measures an optical signal detected by the optical device and converts the optical signal into a digital signal; and a calculator which calculates the amount of the fluorescent material in the microfluidic chip based on a measured value, wherein the calculator acquires a position of an outer circumference of the microfluidic chip from the optical signal detected by the optical device, and calculates a position of the microchamber based on the position of the outer circumference and distance between the outer circumference and the microchamber, and wherein the measuring unit calculates a portion of the optical signal which is generated from the microchamber of the microfluidic chip based on the acquired position of the microchamber, and sends a calculated value of the optical signal portion to the calculator.

2. The fluorescence detection system according to claim 1, wherein the calculator identifies a singular point in an intensity distribution of the optical signal detected by the optical device as the outer circumference of the microfluidic chip.

3. The fluorescence detection system according to claim 2, wherein the singular point is a point in the intensity distribution where the intensity of the optical signal drastically changes.

4. The fluorescence detection system according to claim 1, wherein the microfluidic chip has a plurality of the microchamber,
wherein the calculator acquires a position of an outer circumference of the microfluidic chip from the optical signal detected by the optical device, and calculates positions of the microchambers based on the position of the outer circumference, distances between the outer circumference and the microchambers, and distance between the microchambers, and
wherein the measuring unit calculates portions of the optical signal which are generated from the microchambers of the microfluidic chip based on the acquired positions of the microchambers, and sends calculated values of the optical signal portions to the calculator.

5. The fluorescence detection system according to claim 4, wherein the calculator identifies a singular point in an intensity distribution of the optical signal detected by the optical device as the outer circumference of the microfluidic chip.

6. The fluorescence detection system according to claim 5, wherein the singular point is a point in the intensity distribution where the intensity of the optical signal drastically changes.

7. The fluorescence detection system according to claim 4, wherein the optical device includes a plurality of optical elements each of which emits a unique wavelength light,
wherein the optical element includes:
a light source;
an incident light adjustment lens for collimating the light generated from the light source to be parallel;
an incident light filter for transmitting only a first wavelength light;
an object lens for condensing the light which passed through the incident light filter, emitting the light on the microfluidic chip, and adjusting fluorescence generated from the microfluidic chip to be parallel;
a fluorescence filter for selectively transmitting the fluorescence;
a fluorescence adjustment lens for condensing the light which passed through the fluorescent filter; and
a fluorescence detector for detecting the fluorescence from the light which is condensed by the fluorescence adjustment lens.

8. The fluorescence detection system according to claim 4, wherein the fluorescence detection system measures the amount of fluorescence in a process of polymerase chain reaction (PCR) in the microchamber or the microchambers.

9. The fluorescence detection system according to claim 4, wherein at least two types of dyes are injected into the microchamber or the microchambers, each of the dyes generating a unique wavelength light.

10. The fluorescence detection system according to claim 1, wherein the optical device includes a plurality of optical elements each of which emits a unique wavelength light,
wherein the optical element includes:
a light source;
an incident light adjustment lens for collimating the light generated from the light source to be parallel;
an incident light filter for transmitting only a first wavelength light;
an object lens for condensing the light which passed through the incident light filter, emitting the light on the microfluidic chip, and adjusting fluorescence generated from the microfluidic chip to be parallel;
a fluorescence filter for selectively transmitting the fluorescence;
a fluorescence adjustment lens for condensing the light which passed through the fluorescent filter; and
a fluorescence detector for detecting the fluorescence from the light which is condensed by the fluorescence adjustment lens.

11. The fluorescence detection system according to claim 1, wherein the fluorescence detection system measures the amount of fluorescence in a process of polymerase chain reaction (PCR) in the microchamber or the micro chambers.

12. The fluorescence detection system according to claim 1, wherein at least two types of dyes are injected into the microchamber or the microchambers, each of the dyes generating a unique wavelength light.

13. The fluorescence detection system according to claim 1, wherein the optical device includes a plurality of optical elements each of which emits a unique wavelength light,
wherein the optical element includes:
a light source;
an incident light adjustment lens for collimating the light generated from the light source to be parallel;
an incident light filter for transmitting only a first wavelength light;
an object lens for condensing the light which passed through the incident light filter, emitting the light on the microfluidic chip, and adjusting fluorescence generated from the microfluidic chip to be parallel;
a fluorescence filter for selectively transmitting the fluorescence;
a fluorescence adjustment lens for condensing the light which passed through the fluorescent filter; and
a fluorescence detector for detecting the fluorescence from the light which is condensed by the fluorescence adjustment lens.

14. The fluorescence detection system according to claim 1, wherein the fluorescence detection system measures the amount of fluorescence in a process of polymerase chain reaction (PCR) in the microchamber or the microchambers.

15. The fluorescence detection system according to claim 1, wherein at least two types of dyes are injected into the microchamber or the microchambers, each of the dyes generating a unique wavelength light.

16. A method for detecting fluorescence in a microfluidic chip having at least one microchamber, comprising steps of: injecting a sample and a fluorescent dye into the microchamber; emitting light from an optical device capable of detecting fluorescence on the microfluidic chip, while transporting the micro fluidic chip or the optical device, to detect fluorescence generated from a fluorescent material existing in the micro fluidic chip; and calculating the amount of the fluorescent material in the microfluidic chip based on the amount of the fluorescence detected by the optical device, wherein the step of calculating the amount of the fluorescent material comprises: identifying a position of an outer circumference of the micro fluidic chip based on an optical signal detected by the optical device; calculating a position of the microchamber based on the position of the outer circumference, and a distance between the outer circumference and the microfluidic chamber; and extracting and summing portions of the optical signal generated from the microchamber of the microfluidic chip.

17. The method according to claim 16, wherein the step of calculating a position of the microchamber comprises: calculating positions of each of the microchambers based on intervals between the microchambers.

* * * * *